United States Patent
Rolland et al.

(10) Patent No.: US 8,340,455 B2
(45) Date of Patent: Dec. 25, 2012

(54) SYSTEMS AND METHODS FOR PERFORMING GABOR-DOMAIN OPTICAL COHERENCE MICROSCOPY

(75) Inventors: Jannick Rolland, Orlando, FL (US); Panomsak Meemon, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 939 days.

(21) Appl. No.: 12/415,951

(22) Filed: Mar. 31, 2009

(65) Prior Publication Data
US 2009/0263040 A1    Oct. 22, 2009

Related U.S. Application Data
(60) Provisional application No. 61/040,925, filed on Mar. 31, 2008.

(51) Int. Cl.
  G06K 9/40    (2006.01)
  G01B 9/02    (2006.01)
(52) U.S. Cl. .................................. 382/255; 356/479
(58) Field of Classification Search ........... 382/254–255, 382/284, 299, 312; 600/11, 425, 473; 348/79; 345/629; 356/450, 451, 479
See application file for complete search history.

(56) References Cited

U.S. PATENT DOCUMENTS

| | | | | |
|---|---|---|---|---|
| 4,141,032 A | * | 2/1979 | Haeusler | 348/44 |
| 6,549,801 B1 | * | 4/2003 | Chen et al. | 600/425 |
| 7,242,833 B2 | * | 7/2007 | Yang et al. | 385/117 |
| 7,365,859 B2 | * | 4/2008 | Yun et al. | 356/497 |
| 7,602,501 B2 | * | 10/2009 | Ralston et al. | 356/497 |
| 7,725,169 B2 | * | 5/2010 | Boppart et al. | 600/473 |
| 7,813,788 B2 | * | 10/2010 | Zavislan et al. | 600/476 |

OTHER PUBLICATIONS

Povazay, et al., "Full-Field Time-Encoded Fequency-Domain Optical Coherence Tomography", Aug. 21, 2006/vol. 14, No. 17/Optics Express; pp. 7661-7669.
Holmes, et al., "Multi-channel Fourier Domain OCT system with superior lateral resolution for biomedical applications", Proc. of SPIE vol. 6847, (2008), pp. 1-9.
Holmes, et al., "Theory & application of multi-beam OCT", Proc. of SPIE vol. 7139, (2008), pp. 1-7.

* cited by examiner

*Primary Examiner* — Kanjibhai Patel
(74) *Attorney, Agent, or Firm* — Thomas Horstemeyer, LLP

(57) ABSTRACT

In one embodiment, imaging a medium under evaluation includes generating acquired images of the medium, each acquired image comprising a cross-sectional image along a lateral and a depth direction of the medium that results from scanning the medium at a different depths, filtering each acquired image to remove out-of-focus portions of the images and generate filtered images, and merging the filtered images to form a high-resolution fused image.

26 Claims, 14 Drawing Sheets

SYSTEMS AND METHODS FOR PERFORMING GABOR-DOMAIN OPTICAL COHERENCE MICROSCOPY

CROSS-REFERENCE TO RELATED APPLICATION

This application claims priority to U.S. provisional application entitled, "Gabor Domain Optical Coherence Microscopy," having Ser. No. 61/040,925, filed Mar. 31, 2008, which is entirely incorporated herein by reference.

BACKGROUND

Skin cancer is emerging as the fastest growing type of cancer being reported, especially for the population at or near typical retirement ages. There are three common types of skin cancer: basal cell carcinoma, squamous cell carcinoma, and melanoma. Of the three, melanoma is the most dangerous because it is the variant most likely to metastasize and spread to the rest of the body.

Early detection of skin cancer is critical to preventing such spreading. Presently, the most reliable test for skin cancer is a skin biopsy. Unfortunately, however, diagnosing skin cancer from an excised sample of skin can be disadvantageous. For example, because the excised sample is small and the dissection of the sample is random, a diagnosis based on biopsy may be inaccurate. Moreover, if a cancer diagnosis is made, the patient may be required to return for further biopsies until the extent of the cancer is determined, resulting in multiple biopsy procedures and, potentially, the unnecessary removal of healthy skin. In addition, complications can arise as a result of biopsy, such as infection, hemorrhage, and the spreading of cancer cells.

Furthermore, no imaging technology currently exists that can be used to accurately identify the extent of cancerous lesions for purposes of surgical resection. Although optical coherence tomography (OCT) and optical coherence microscopy (OCM) have emerged as noninvasive technologies that show promise for replacing skin cancer diagnosis via biopsy, neither has been able to provide histological level resolution throughout the region that can contain early developing anomalous cells. OCT technology has evolved to provide nearly constant 15-20 micron (μm) resolution to depths of approximately 1 millimeter (mm) in scattering media like skin, but the histological examination of a biopsy provides information typically based on the structure of 1-5 μm features. OCM can provide 1-5 μm resolution, but only over a few tens of microns of depth, not the hundreds of microns that are needed. Therefore, neither OCT nor OCM, in their current forms, have removed the need for biopsy.

BRIEF DESCRIPTION OF THE FIGURES

The present disclosure may be better understood with reference to the following figures. Matching reference numerals designate corresponding parts throughout the figures, which are not necessarily drawn to scale.

DETAILED DESCRIPTION

Figure 1:
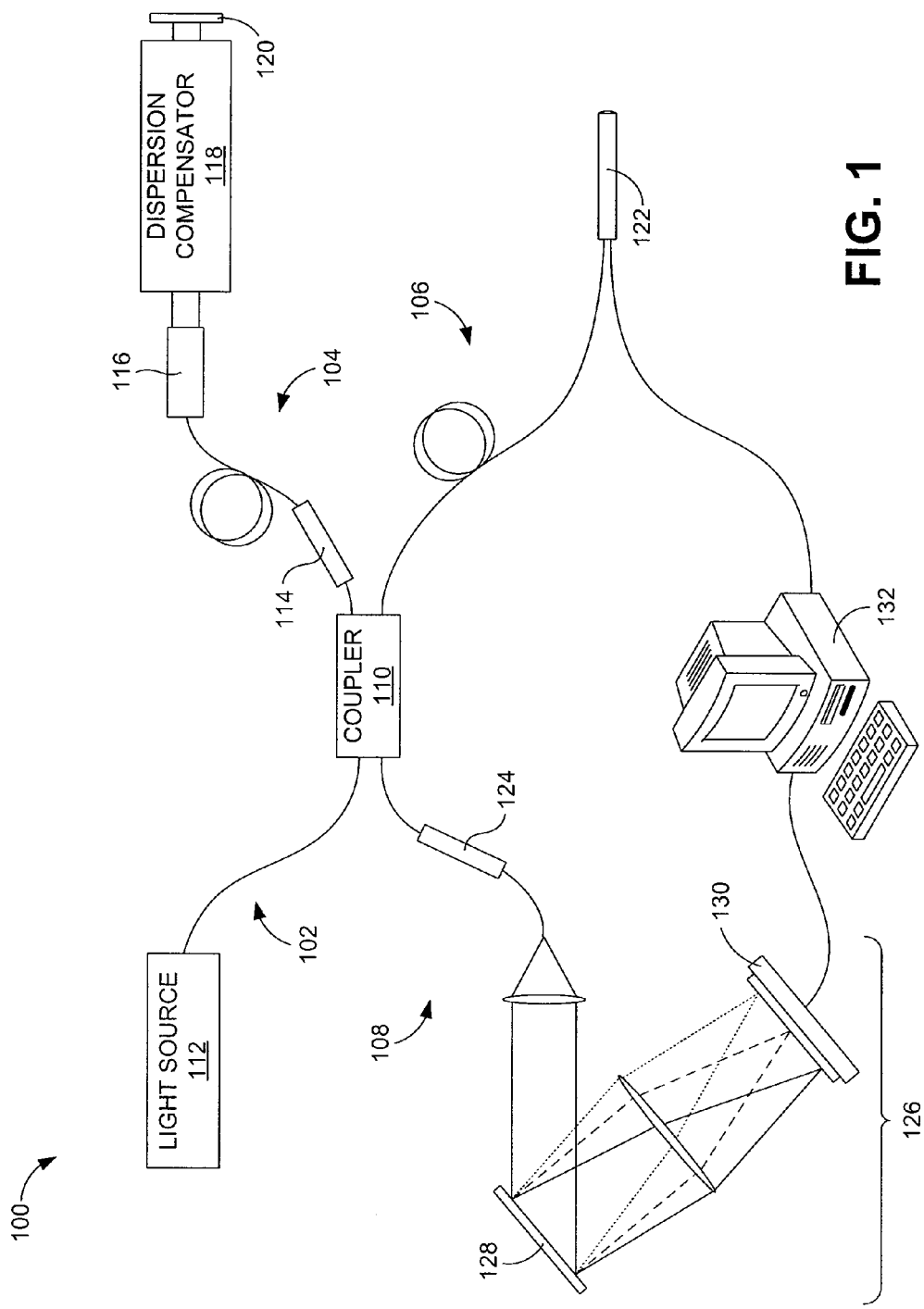
FIG. 1 is a block diagram of an embodiment of a system for performing Gabor-domain optical coherence microscopy.

As described above, there are currently no imaging technologies suitable for skin cancer detection or determining the physical expanse of the disease even though both optical coherence tomography (OCT) and optical coherence microscopy (OCM) have shown promise as possible optical detection technologies. The principle of OCT was first demonstrated in 1991. Because the lateral resolution for OCT was not as high as desired, early advances in time-domain OCT (TD-OCT) included increasing the numerical aperture of the optics in an attempt to improve lateral resolution, which resulted in the creation of time-domain OCM (TD-OCM). Although increasing the numerical aperture did improve lateral resolution, it also reduced the ability to gather data over significant depths given that the lateral resolution improved the focus of the beam of light but worsened outside the depth of focus region. Later, researchers attempted to improve the speed of imaging in OCT with the introduction of Fourier-domain OCT (FD-OCT) and the related swept-source OCT (SS-OCT). Both FD-OCT and SS-OCT operate on the principle of spectral-domain OCT (SD-OCT), where the full depth profile of the sample reflectivity is achieved by inverse Fourier transform of an acquired spectral interference signal as opposed to a measured intensity per point scanned as in TD-OCT. SD-OCT attracted significant interest because of its improved sensitivity and imaging speed when compared to TD-OCT. Still, the issue of lack of lateral resolution in OCT images remained to be solved.

The next step forward in improving lateral resolution was the addition of real-time mechanical focusing in which a reference mirror and a focusing lens were mounted together on a common translation stage to create dynamic focusing TD-OCM (DF-TD-OCM), which achieved resolutions of approximately 10 microns (μm) axially and approximately 4 μm laterally with a 1 millimeter (mm) depth at 8.5 A-scans/second. DF-TD-OCM was demonstrated by using an optical setup that shifts the focus through a longitudinal magnification. Unfortunately, the depth of focus is intrinsically limited in such an approach.

Still later, a related technique to dynamic focusing was investigated called zone focusing. In that technique, individual layers in depth are imaged, each depth with a new focusing of the beam in that layer. An image fusion technique similar to that performed with C-mode scanning in ultrasound was then applied in which tomograms from different layers were fused to form a high-resolution image over an extended depth. A high resolution of 1.5 µm axially and 3 µm laterally was demonstrated by manually changing focus before acquiring the image of the new zone, which prohibited application to in vivo imaging. More recently, three dimensional C-mode OCM imaging was proposed using a high-speed, frequency swept 1300 nanometer (nm) source and C-mode scanning (i.e., zone focusing). However, the C-mode scanning was implemented by a stage with a C-scanning translation stage.

To date, attempts at implementing high lateral resolution OCM without scanning stages (a critical requirement for moving the technology outside of the laboratory) have failed due to shortcomings in the optical designs. What is needed is a technology to step through focus (without moving stages) up to depths of at least 0.5 mm and possibly up to 2 mm while maintaining high axial and lateral resolution (i.e., less than approximately 3 µm). The above developments have inspired a solution referred to herein as Gabor-domain OCM (GD-OCM), which provides a data collection timeline and process targeted for high axial and lateral resolution imaging at speeds that are adapted for two-dimensional (2D) and three-dimensional (3D) in vivo clinical imaging.

Disclosed herein are systems and methods for performing GD-OCM. In some embodiments, spectral interference signals are collected from a medium, such as skin, at in vivo imaging speeds using an optical instrument capable of laterally scanning at discrete depths to produce 2D images of a cross-section of the medium. Once each image has been generated, the images are processed to automatically filter out-of-focus areas in the images to produce filtered images each comprising an in-focus portion of the entire cross-section, which pertains to a discrete portion (i.e., range of depth) of the medium. The filtered images are then automatically merged to generate a fused image of the medium cross-section having invariant, high resolution (i.e., resolution less than approximately 3 µm).

FIG. 1 illustrates an example embodiment of a system 100 for performing GD-OCM. As is apparent from FIG. 1, the system 100 has the basic configuration of an interferometer and therefore generally comprises a source arm 102, a reference arm 104, a sample arm 106, and a detector arm 108, each of which can comprise one or more optical fibers and each of which being coupled to an optical coupler 110, which in some embodiments comprises an 80/20 fiber coupler. Associated with the source arm 102 is a light source 112, which can comprise a high-power broadband Ti:Sa laser. By way of example, the light source 112 is a 120 nm full width at half maximum (FWHM) laser centered at 800 nm.

The reference arm 104 includes a polarization controller 114, a collimator 116, a dispersion compensator 118, and a mirror 120. Associated with the sample arm 106 is an optical instrument 122 that is used to collect backscattered light from a medium under evaluation, such as human skin. In some embodiments, the optical instrument 122 is configured as a handheld probe having a tip that can be applied to an outer surface of the medium. The detector arm 108 includes a further polarization controller 124 and is associated with a detector 126. In the illustrated embodiment, the detector 126 is configured as a spectrometer that comprises a diffractive grating 128 and an image sensor 130, such as a charge-coupled device (CCD) or CMOS array.

As is further illustrated in FIG. 1, the system 100 includes a computer system 132 that receives and processes data from the detector 126. In addition, the computer system 132 can be used to control the optical instrument 122. In some embodiments, the computer system 132, as suggested by FIG. 1, comprises a single computer. In alternative embodiments, however, the computer system 132 can comprise two or more individual computers that operate in conjunction with each other, for example in a networked arrangement.

During operation of the system 100, light generated by the light source 112 is transmitted to both the mirror 120 via the reference arm 104 and to the optical instrument 122 via the sample arm 106. The light signals reflected back from mirror 120 and from structures within the medium under evaluation are then transmitted to the detector 126, which processes the interfered signals. A resulting spectral intensity is then output from the detector 126 to the computer system 132 for further processing described in detail below.

Figure 2:
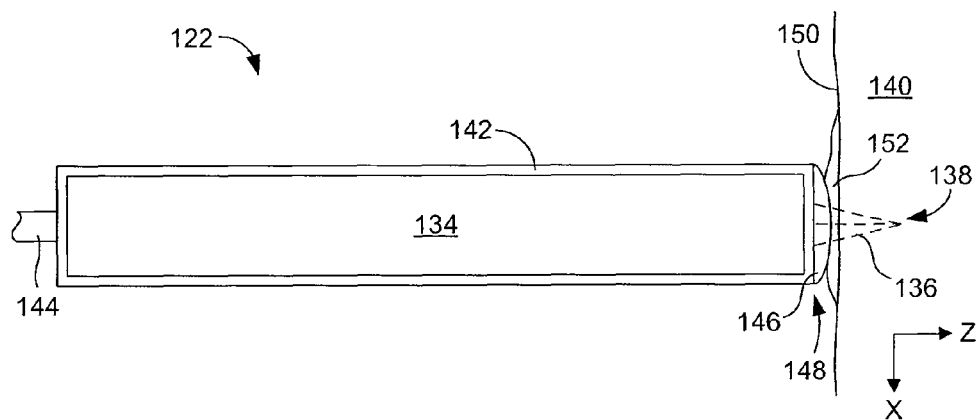
FIG. 2 is a schematic side view of an embodiment of an optical instrument used in the system of FIG. 1.

FIG. 2 is a block diagram of an embodiment of the optical instrument 122 shown in FIG. 1. As indicated in FIG. 2, the instrument 122 includes an internal optical system 134 that focuses light 136 on a focus point 138 of a medium under evaluation 140. The light 136 is backscattered by structures (not shown) within the medium 140 and is reflected back to the optical system 134.

The optical instrument 122 further includes a housing 142 that contains the optical system 134. Extending from a proximal end of the housing 142 is a cord 144 that transmits light from the light source 112 (FIG. 1) to the optical system 134 and transmits reflected light to the detector 126 (FIG. 1). By way of example, the cord 144 includes a fiber optic fiber or cable (not shown). The cord 144 can also comprise one or more electrical wires (not shown) that connect the instrument 122 to the computer system 132 (FIG. 1). An imaging window 146 is provided at a distal end 148 of the instrument 122 that acts as an interface between the instrument and the medium 140. To limit the tendency of a surface 150 of the medium 140 to reflect the transmitted light 136 back to the optical system 134, an immersion material 152, such as an oil or gel, having approximately the same refractive index as the medium can be placed between the imaging window 146 and the medium.

To facilitate the performance of GD-OCM, the optical instrument 120 both laterally and axially scans the medium 140 by focusing the light 136 at discrete focus points 138 in the lateral and axial directions. The light signals backscattered by the structures of the medium 140 are provided to the detector 126 (FIG. 1) and are used to reconstruct images of the medium. The images comprise 2D cross-sectional images of the medium 140 that extend along the lateral and axial directions of the medium, or the x and z directions, respectively, in FIG. 2. For purposes of this disclosure, the term "lateral" refers to the direction that is substantially parallel to the surface 150 of the medium 140 (i.e., the x direction in FIG. 2). Therefore, "lateral scanning" comprises scanning the medium 140 in a direction generally parallel to the medium surface 150. The term "axial" refers to a direction that is substantially perpendicular to the surface 150 of the medium (i.e., the z direction in FIG. 2). Therefore, "axial scanning" comprises scanning the medium 140 in a direction generally perpendicular to its surface 150.

Figure 3:
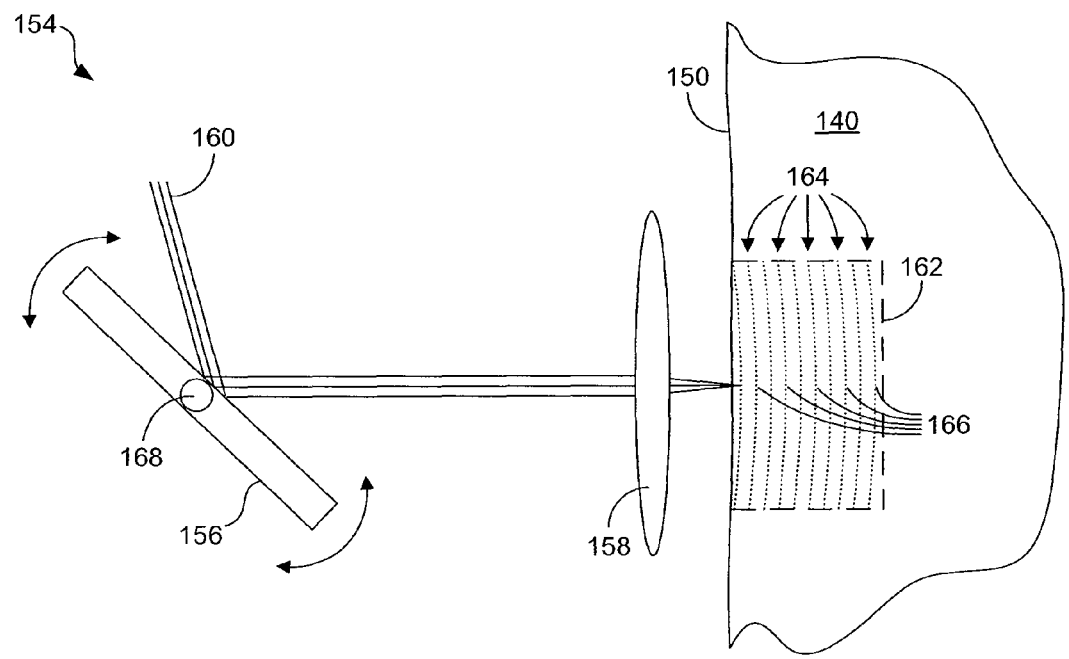
FIG. 3 is a schematic side view of an embodiment of an optical system that can be used in the optical instrument of FIG. 2.

FIG. 3 is a side view of a first embodiment of an optical system 154 that can be used in the instrument 122 of FIG. 2. The optical system 154 includes a scanning element 156 and a variable focus lens 158 that together laterally and axially scan light 160 relative to the medium 140. Lateral scanning is accomplished by actuating the scanning element 156, which redirects the light 160 to laterally adjacent points of the medium 140 along a chosen lateral scan 164. Axial scanning is accomplished by readjusting the variable focus lens 158 to alter the focal length of the lens, such that the lens is focused at a desired axial depth 166. In some embodiments, an entire cross-section 162 of the medium 140 can be scanned by focusing a first depth 166, collecting spectra at discrete lateral positions (i.e., x positions) at that depth, adjusting the variable focus lens 158 to focus at a new (e.g., deeper) depth 166, collecting spectra at discrete lateral positions (i.e., x positions) at that new depth, and so forth until complete lateral scans have been performed at the desired number of depths. The number of lateral positions and depths at which spectra are collected can be selected by the user in relation to desired acquisition speed and resolution. By way of example, acceptable results can be obtained by collecting spectra at approximately 100 lateral positions (i.e., x positions) at each of approximately 10 different depths (i.e., z positions), in which case spectra are collected at 1,000 different focus points 138 (FIG. 2).

The scanning element 156 can comprise a scanning mirror, such as a micro-electro-mechanical-system (MEMS) mirror or a galvo mirror. Regardless, the scanning element 156 may have an axis 168 about which the element can be rotated, as depicted in FIG. 3. In other embodiments, the scanning element 156 can rotate about two axes (not shown) or the optical system 154 can have two single-axis scanning elements (not shown) to enable scanning in multiple directions.

In some embodiments, the variable focus lens 158 is a lens that refocuses without mechanical translation, i.e., without being physically moved. Such a lens remains axially stationary, unlike conventional systems that refocus by axially translating bulk optics. Examples of lenses that do not mechanically translate include liquid lenses and liquid crystal lenses. The response time of such a lens may be on the order of tens of milliseconds (ms).

Figure 4A:
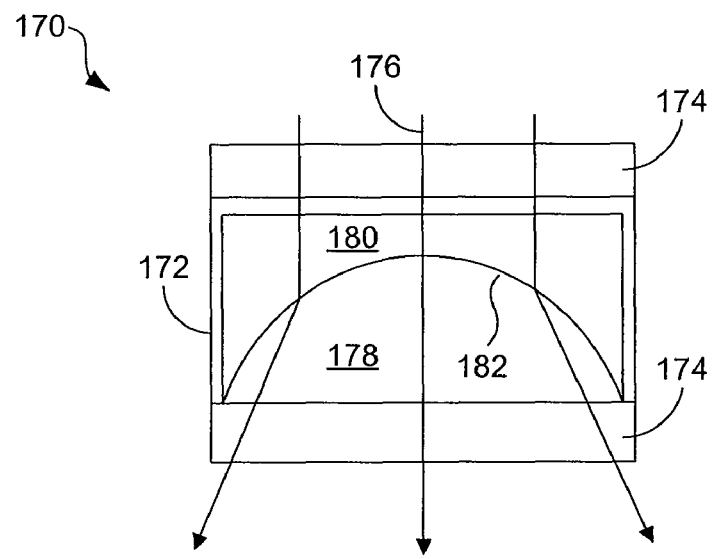
FIGS. 4A and 4B are schematic side views of an embodiment of a variable focus lens that can be used in the optical system of FIG. 3, each figure illustrating the lens at a different focus setting.
Figure 4B:
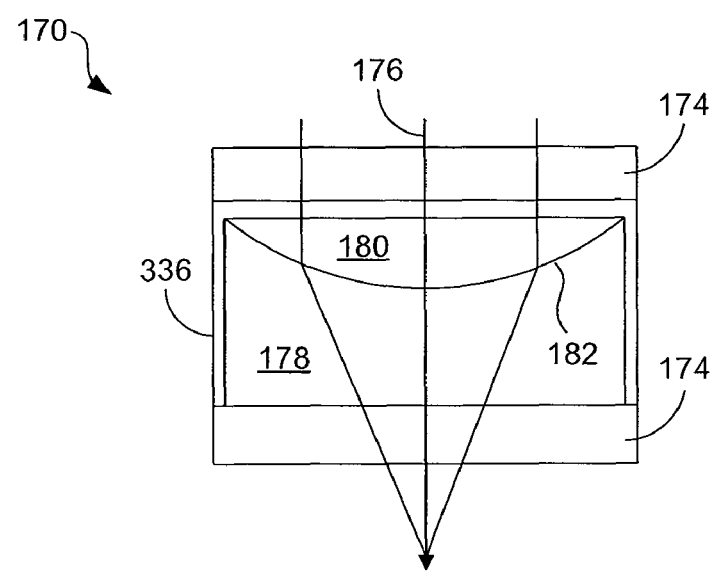

FIG. 4A is a side view of an embodiment of a liquid lens 170 that can be used in the optical system 154 shown in FIG. 3. The liquid lens 170 comprises a tubular casing 172 with transparent end caps 174. Light 176 may pass through a first end cap 174 into the lens 170 and then out of the lens through a second end cap 174. Within the tubular casing 172 are a first liquid 178 and a second liquid 180. The liquids 178 and 180 are immiscible liquids having approximately the same density but different refractive indexes. In some embodiments, the first liquid 178 is electrically conductive and the second liquid 180 is nonconductive. For example, the first liquid 178 can be an electrically-conductive aqueous solution and the second liquid 342 can be a nonconductive oil. Because the liquids 178 and 180 are immiscible with respect to each other, a meniscus 182 forms between the two liquids, and a radius of curvature of the meniscus determines the focal length of the lens 170. The liquid lens 170 can be refocused by altering the radius of curvature of the meniscus 182, which may be accomplished by applying a voltage to a hydrophobic coating (not visible) that covers the interior of the tubular casing 172 and one of the end caps 174. Applying a voltage alters the hydrophobicity of the coating causing the electrically conductive first liquid 178 to become more or less resistant to the hydrophobic coating. As the first liquid 178 moves into greater or lesser contact with the hydrophobic coating, the radius of curvature of the meniscus 182 changes and the focal length of the lens 170 is adjusted, as shown in FIG. 4B. Therefore, the liquid lens 170 can be refocused electrically, unlike a conventional lens that refocuses by mechanical translation. Liquid lenses of the type illustrated in FIGS. 4A and 4B may be acquired from Philips Corporation and Varioptic, Inc.

Figure 5:
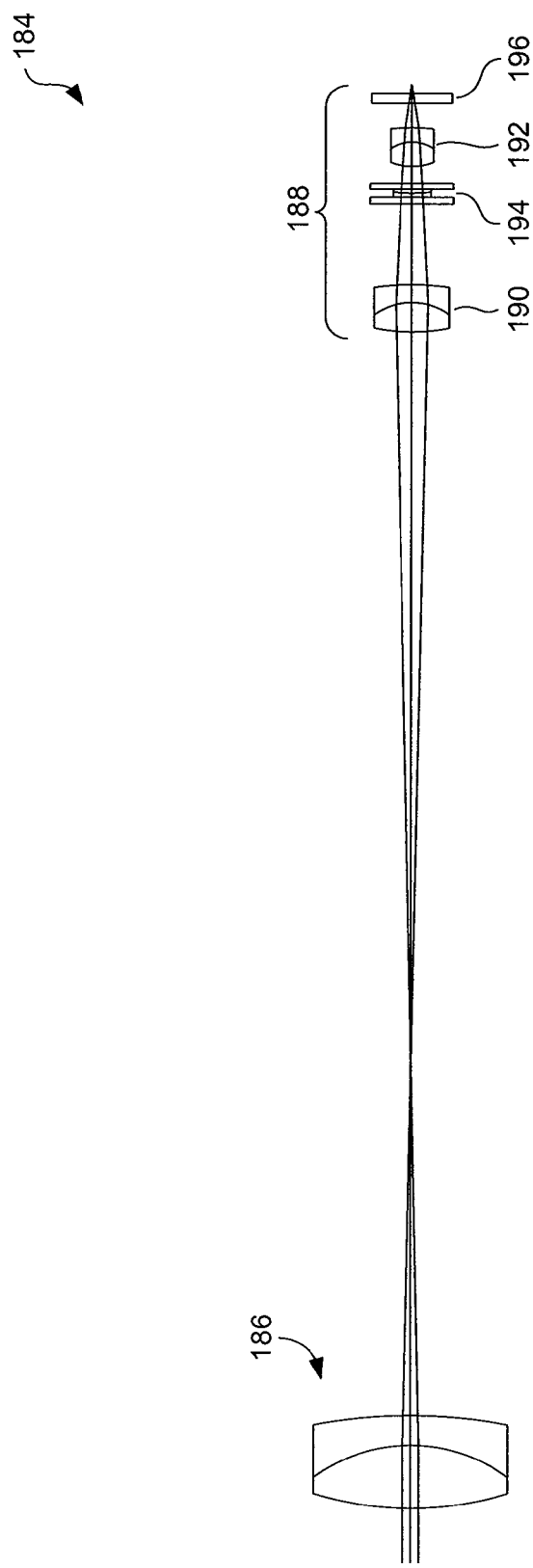
FIG. 5 is a side view of a further embodiment of an optical system that can be used in the optical instrument of FIG. 2.

FIG. 5 is a side view of a further embodiment of an optical system 184 that can be used in the optical instrument 122 of FIG. 2. The optical system 184 includes a scan lens 186 and an objective 188. Although not shown in FIG. 5, the optical system 184 can further include a scanning element similar to that used in the optical system 154. In embodiments in which imaging across three dimensions is not desired, a single-axis scanning element may be used instead of a dual-axis scanning element because a single-axis scanning element rotates at a relatively faster rate than a dual-axis scanning element.

As illustrated in FIG. 5, the scan lens 186 can comprise a doublet lens. Alternatively, the scan lens 186 can comprise a simple lens. Regardless, angles of the rays exiting the scan lens 186 are controlled to match the entry rays of the optical system 184. As the magnification of the system 184 increases, the complexity of the scan lens 186 can also increase or multiple optical elements may be used. In the embodiment of FIG. 5, the objective 188 comprises three optical elements, including first and second doublet lenses 190 and 192 and a variable focus lens 194, as well as an imaging window 196, which is placed in contact with the medium under evaluation. In the illustrated embodiment, the variable focus lens 194 comprises a liquid lens that includes two immiscible liquids held between and two clear plates.

Figure 6:
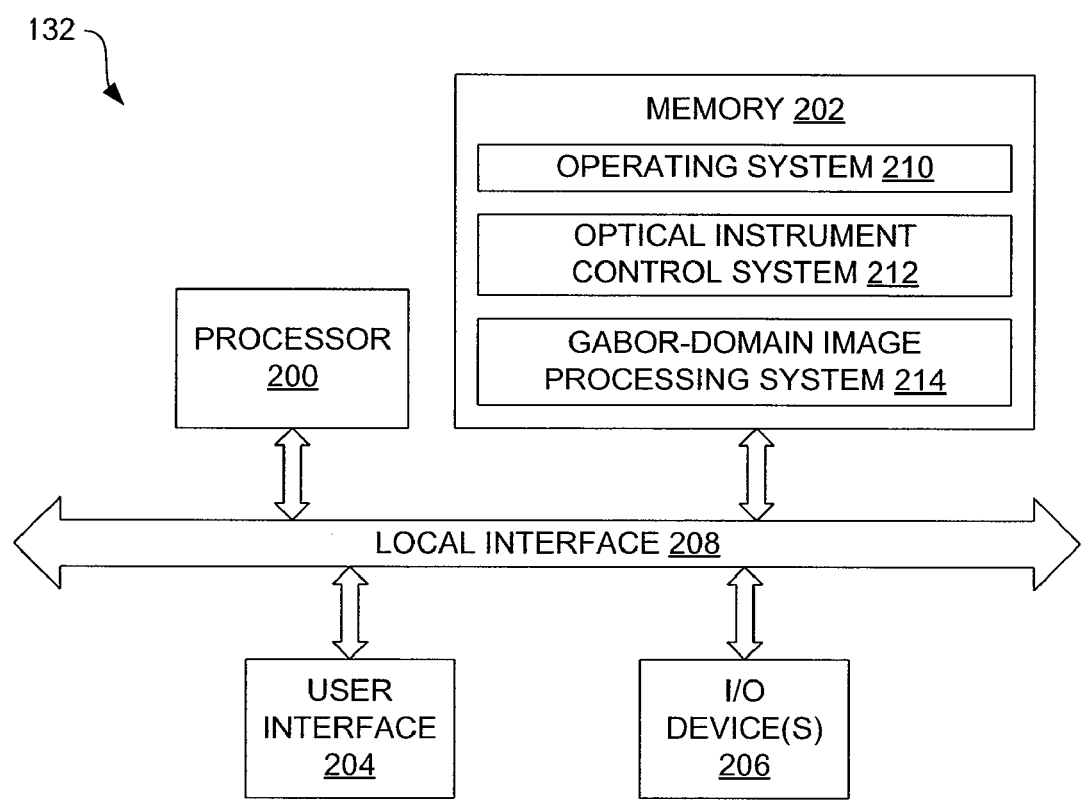
FIG. 6 is a block diagram of an embodiment of a computer system used in the system of FIG. 1.

FIG. 6 is a block diagram illustrating an example architecture for the computer system 132 shown in FIG. 1. In the embodiment of FIG. 6, the computer system 132 comprises a processing device 200, memory 202, a user interface 204, and at least one input/output (I/O) device 206, each of which is connected to a local interface 208.

The processing device 200 can include a central processing unit (CPU) or a semiconductor-based microprocessor. In addition, the processing device 200 can include one or more graphical processing units. The memory 202 includes any one of a combination of volatile memory elements (e.g., RAM) and nonvolatile memory elements (e.g., hard disk, flash memory, ROM, etc.).

The user interface 204 comprises the components with which a user interacts with the computer system 132. The user interface 204 can comprise, for example, a keyboard, mouse, and a display. The one or more I/O devices 206 are adapted to facilitate communications with other devices and can include one or more communication components, such as a wireless (e.g., radio frequency (RF)) transceiver, a network card, etc.

The memory 202 stores various programs including an operating system 210, an optical instrument control system 212, and a Gabor-domain image processing system 214. The operating system 210 controls the execution of other programs and provides scheduling, input-output control, file and data management, memory management, and communication control and related services. The optical instrument control system 212 is controls operation of the optical instrument 122 (FIG. 1). Finally, the Gabor-domain image processing system 214 automatically processes acquired cross-sectional images of a medium under evaluation. As described in greater detail below, such processing includes filtering of out-of-focus image data and merging filtered images to produce a fused image having invariant high resolution (i.e., resolution less than approximately 5 µm). Examples of operation of the Gabor-domain image processing system 214 are described in relation to FIGS. 7-13.

The mathematical basis for the filtering and fusing performed by the Gabor-domain image processing system 214 will now be discussed. Consider a typical spectral domain OCT configuration. A spectral intensity as detected by a spectrometer can be modeled as $$\hat{I}_D(k)=\hat{S}(k)\cdot(|r_R|^2+2r_R\int r_S(l_S)\cos(2k(l_S-l_R))dl_S+|\int r_S(l_S)e^{ikl_S}dl_S|^2) \quad (1)$$

where the caret denotes a function in the spectral domain, $\hat{I}_D(k)$ is the detected spectral intensity $\hat{S}(k)$ is the power spectral density of the source, $l_R$ and $l_s$ are round-trip optical path lengths along the reference and sample arms respectively, $r_R$ is the reflectivity of the reference mirror, $r_S(l_S)$ represents the sample reflectivity profile along the depth. For purposes of simplification, it can be assumed that the DC and auto-correlation terms (1$^{st}$ and 3$^{rd}$ terms) can be removed. Since only the optical path length difference is of interest, the optical path difference is defined as $l_D=l_S-l_R$, and hence the spectral interference signal, can then be expressed as $$\hat{I}_{int}(k)=2r_R\hat{S}(k)\cdot\int r_S(l_D)\cos(2kl_D)dl_D \quad (2)$$

where $r_S(l_D)$ now represent the sample reflectivity profile as a function of the optical path length difference $l_D$. Inverse Fourier transform of Equation (2) yields $$I_{OCT}(l_D)=\mathfrak{I}^{-1}\{\hat{I}_{int}(k)\}=r_R\mathfrak{I}^{-1}\{\hat{S}(k)\}*[r_S(l_D)+r_S(-l_D)] \quad (3)$$

Equation (3) reveals that the sample reflectivity profile along the depth direction can be achieved by the inverse Fourier transform (IFT) of the measured spectral interference signal, which is a fundamental principle of Fourier Domain OCT (FD-OCT). The term $r_S(-l_D)$ is known as mirror image or ghost image in FD-OCT.

Next consider the Gabor transform, which is simply a local Fourier transform defined by $$\hat{F}(k;z_0)=\int_{-\infty}^{\infty}f(z)g(z-z_0)\exp(ikz)dz, \quad (4)$$

where $g(z-z_0)$ is a sliding window function with arbitrary shape, such as rectangular or Gaussian shape. The function is usually chosen to be concentrated around $z=z_0$. The function $g(z-z_0)$ typically has a finite width, which is narrower than the function $f(z)$. Therefore, $F(k;z_0)$ represents the local frequency components of the function $f(z)$ within the width of the sliding window $g(z-z_0)$. Applying Equation (4) to Equation (3), the Gabor transform of the interference signal is $$\hat{I}_G(k;l_G)=\int I_{OCT}(l_D)g(l_D-l_G)\exp(ikl_D)dl_D, \quad (5)$$

$$\hat{I}_G(k;l_G)=\hat{I}_{int}(k)*[\mathfrak{I}\{g(l_D)\}\cdot\exp(ikl_G)] \quad (6)$$

where $l_G$ is the shifted distance of the center of the window in spatial domain. Using the definition $\hat{G}(k;l_G)=\mathfrak{I}\{g(l_D)\}\cdot\exp(ikl_G)$, $\hat{I}_G(k;l_G)$ is a convolution between the spectral interference $\hat{I}_{int}(k)$ and $\hat{G}(k;l_G)$. Therefore, an inverse Fourier transform of $I_G(k;l_G)$ yields a multiplication between the sample reflectivity profile and the sliding window in the spatial domain.

To extract only the in-focus portion of the acquired image, one can multiply an acquired GD-OCM image with a sliding window whose width is defined corresponding to the depth of focus and whose center is shifted to the focal plane of the objective lens. Combining this technique with an ability to re-focus while acquiring a multiple FD-OCM images, the portion of the cross-sectional image around each focus position can be extracted and then fused to form a quasi-invariant resolution image. The procedure to extract the in-focus portion is equivalent to an inverse process of the Gabor transformation.

Figure 7:
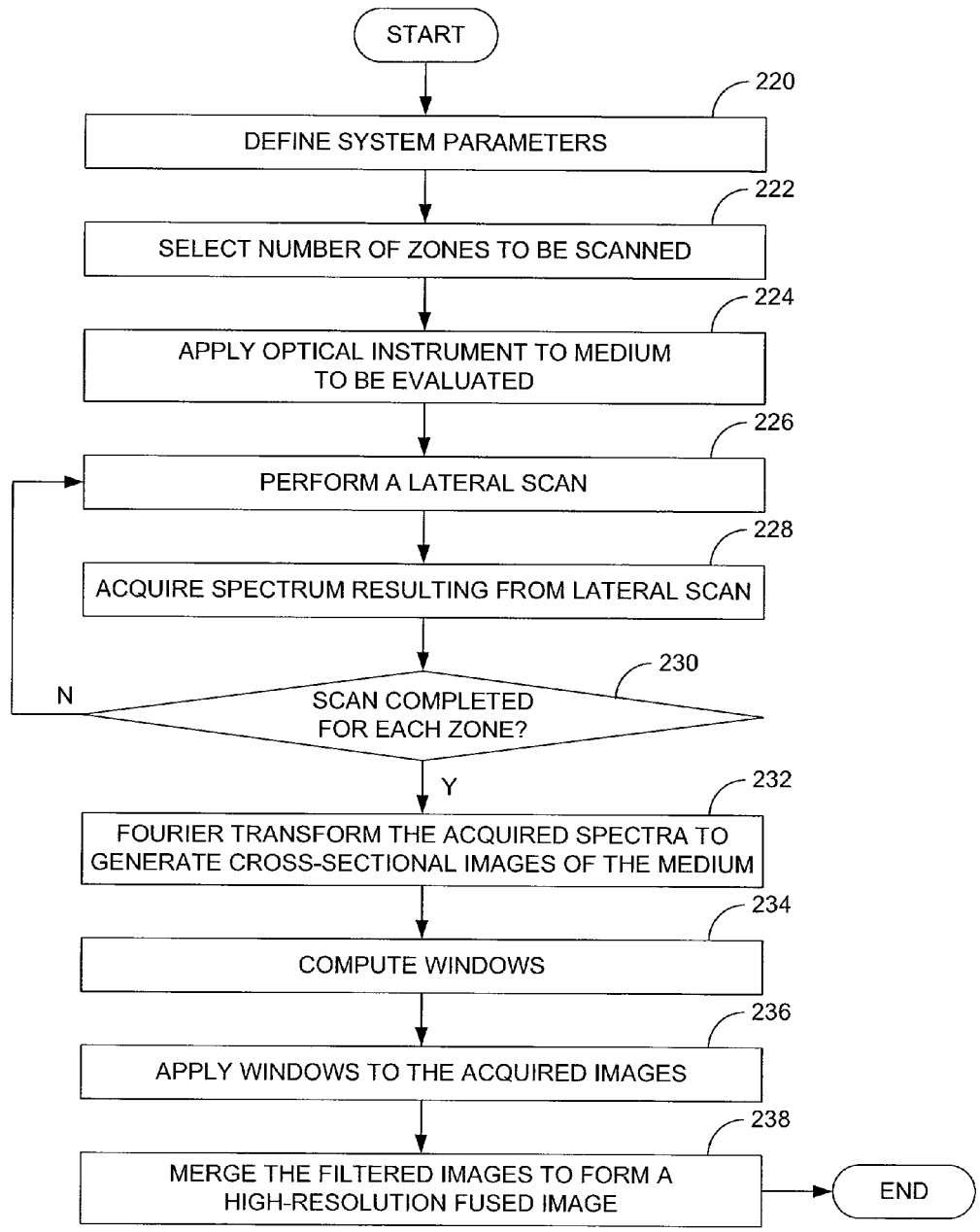
FIG. 7 is a flow diagram of an embodiment of a method for performing Gabor-domain optical coherence microscopy.

FIG. 7 describes an embodiment of a method for performing GD-OCM and the associated processing performed by the Gabor-domain image processing system 214. Beginning with block 220 of FIG. 7, the parameters of the system can first be defined. Such parameters can include, for example, the number of points at which to focus during a lateral scan, the speed at which scanning is to be performed, the DC removal method to be applied, the averaged index of refraction of the medium, the exposure time of the sensor and so forth. Next, with reference to block 222, the number of zones to be scanned can be selected. That is, the number of depths (i.e., z positions) at which lateral scanning is to be performed can be selected. In some embodiments, the number of zones selected depends upon the depth of the medium under evaluation that is to be imaged and the depth of focus achievable with the optical system of the instrument that for each focus group. For example, if it is desired to image a region extending from the surface of the medium to a depth of 1 mm under the surface, and the optical system is capable of collecting in-focus image data across a range of 100 μm (i.e., 0.1 mm), it would be prudent to set the number of zones to 10 so that in-focus data can be collected across the entire 1 mm depth.

Referring next to block 224, the optical instrument (e.g., instrument 122 of FIG. 1) is applied to the medium to be evaluated. The instrument can then be activated to perform a lateral scan, as indicated in block 226, and spectra resulting from the scan can be collected, as indicated in block 228. During each lateral scan, a spectrum of light is collected at each of multiple (e.g., 100) discrete lateral positions (x positions) at a given zone. Once a spectrum has been collected at each discrete lateral position, the inverse Fourier transform of a set of acquired spectra can be combined to form a 2D image of a cross-section of the medium under evaluation. Therefore, a separate cross-sectional image can be generated for each lateral scan. In keeping with the previous example, if 10 zones were selected in block 222, 10 cross-sectional images could then be generated.

Referring next to decision block 230, it is determined whether a lateral scan has been performed for each zone. If not, flow returns to block 226 and the next lateral scan is performed. By way of example, the next lateral scan is performed at the next deeper zone of the medium under evaluation. The data acquisition described in relation to blocks 226-230 continues until the point at which the final lateral scan has been performed. At that point, flow continues to block 232 at which the acquired spectra are Fourier transformed to generate cross-sectional images of the medium. Examples of such cross-sectional images, also referred to herein as "acquired" images, are shown in FIGS. 9A-9F. In those figures, the horizontal direction of the images corresponds to the lateral direction of the medium, and the vertical direction of the images corresponds to the depth direction of the medium. Given that there are a total of six acquired images in the example of FIGS. 9A-9F, lateral scans were performed at six different zones or depths.

As described above, the lateral scans are performed by focusing light at discrete lateral points along multiple depths of the medium under evaluation. When the depth of the medium that is to be imaged exceeds the depth of focus of the optical system that is used to acquire the spectra, out-of-focus image data will be collected. This phenomenon is visible in FIGS. 9A-9F. Specifically, shallow features of the medium appear more in focus in images generated during shallower lateral scans and deeper features of the medium appear more in focus in images generated during deeper lateral scans. For example, features are clearly visible in the top portion of the acquired image of FIG. 9A, which was generated using spectra from the shallowest lateral scan, while those same features are less clear in the acquired image of FIG. 9B, which was generated using spectra from the deepest lateral scan. In view of this, each acquired image contains in-focus portions and out-of-focus portions, and a final high-resolution image of the entire cross-section could be generated by merging the in-focus portions of each acquired image. As described above, this can be achieved by filtering out the out-of-focus portions using sliding windows. With reference to block 234 of FIG. 7, the windows are first computed.

Figure 8:
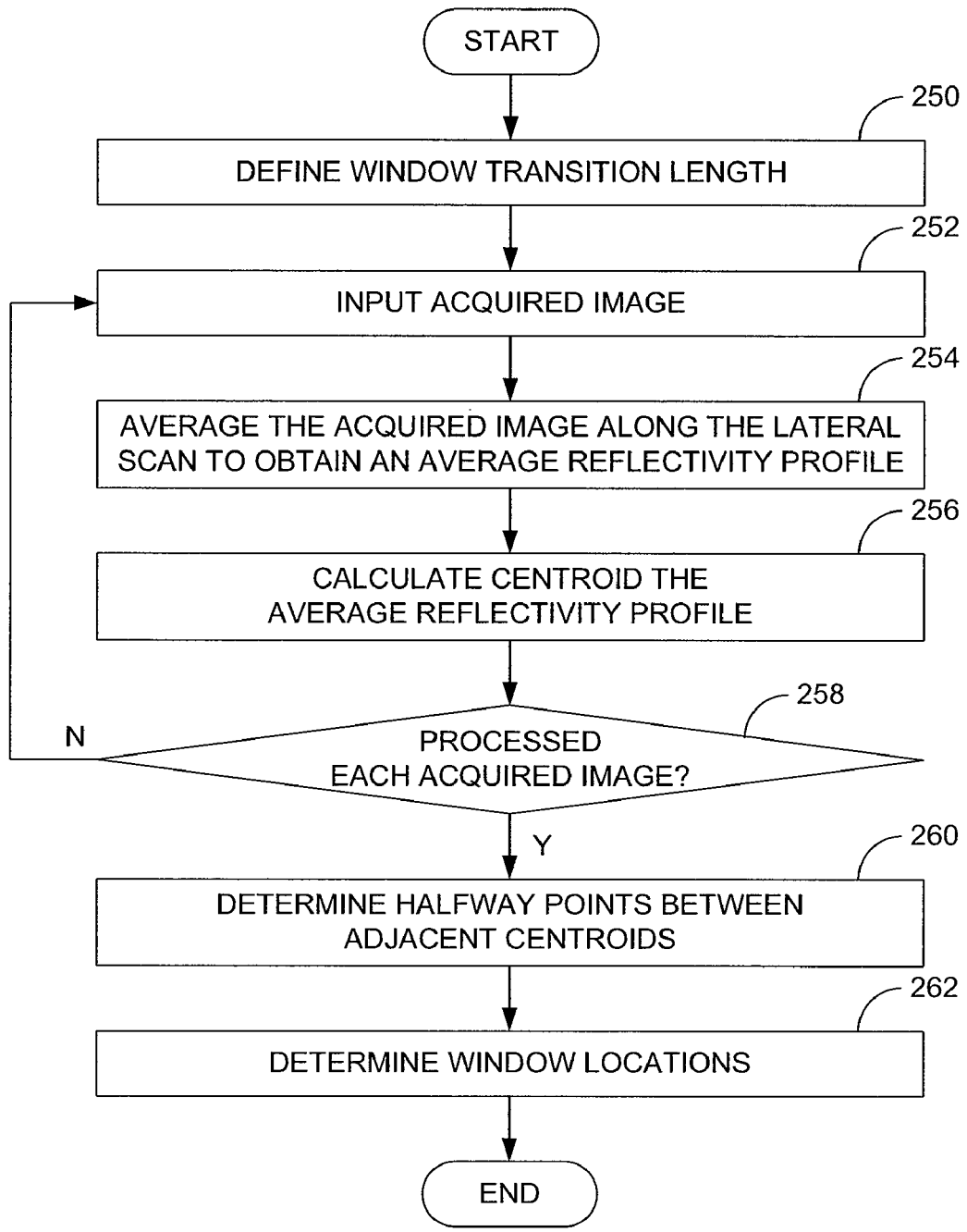
FIG. 8 is a flow diagram of an embodiment of a method for computing windows used in the method of FIG. 7.
Figure 9A:
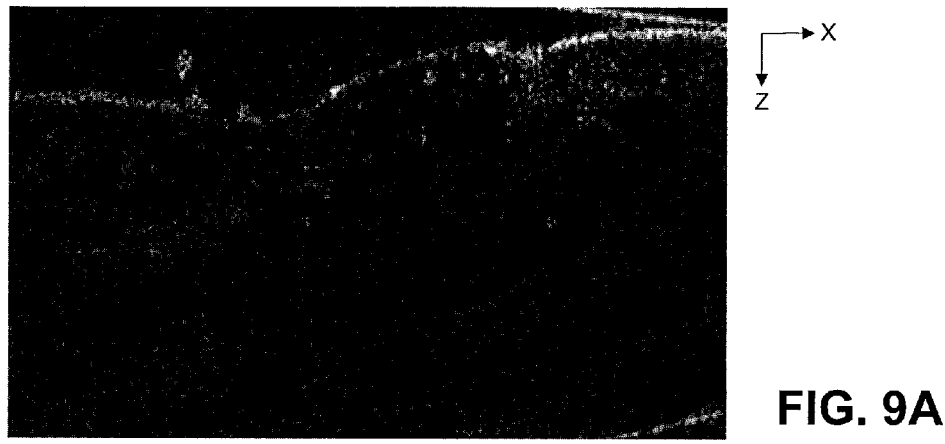
FIGS. 9A-9F are example acquired images of a cross-section of a medium under evaluation, each image being acquired by focusing at a different depth of the medium.
Figure 10A:
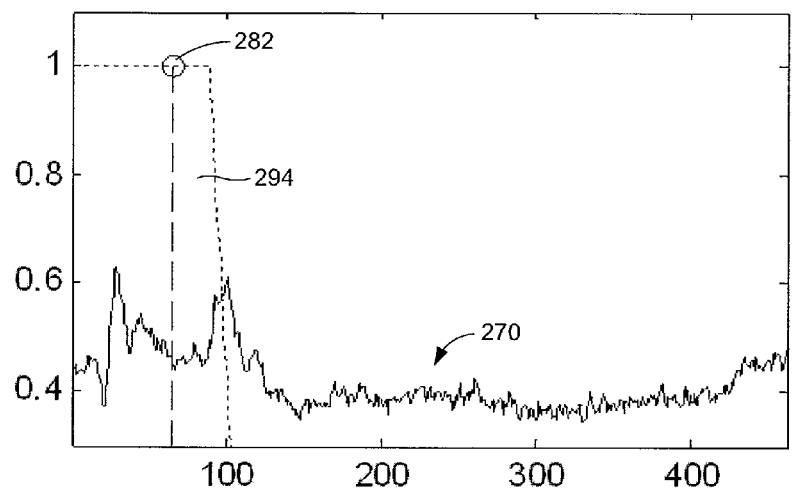
FIGS. 10A-10F plot averaged reflectivity profiles for the acquired images of FIGS. 9A-9F, and further identify windows associated with the profiles for use in filtering out-of-focus portions of the acquired images.
Figure 11A:
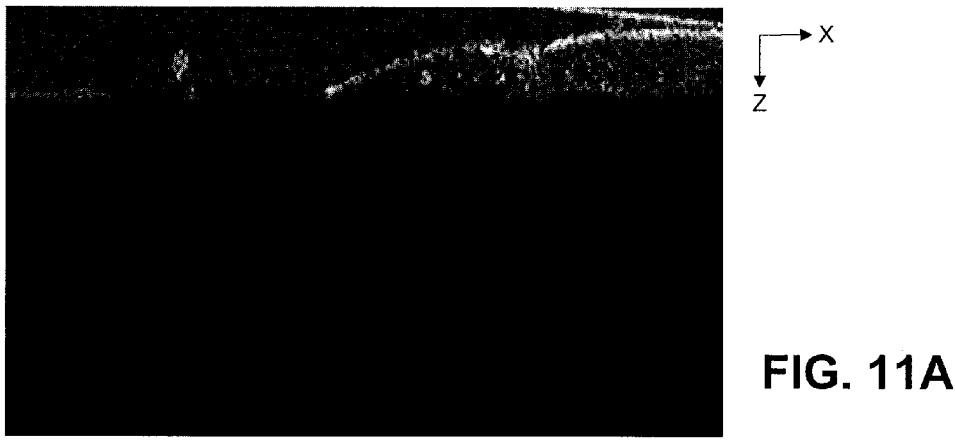
FIGS. 11A-11F are filtered images that result when the windows of FIGS. 10A-10F have been applied to the acquired images of 9A-9F to remove the out-of-focus portions of the acquired images.
Figure 9B:
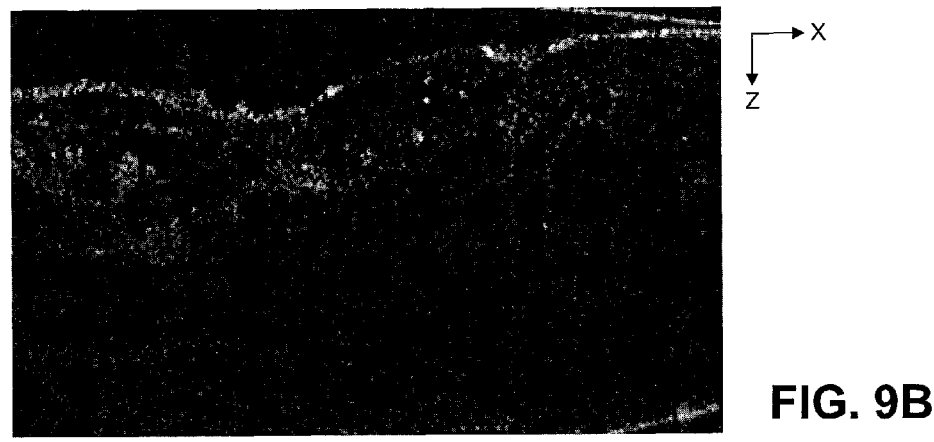
Figure 10B:
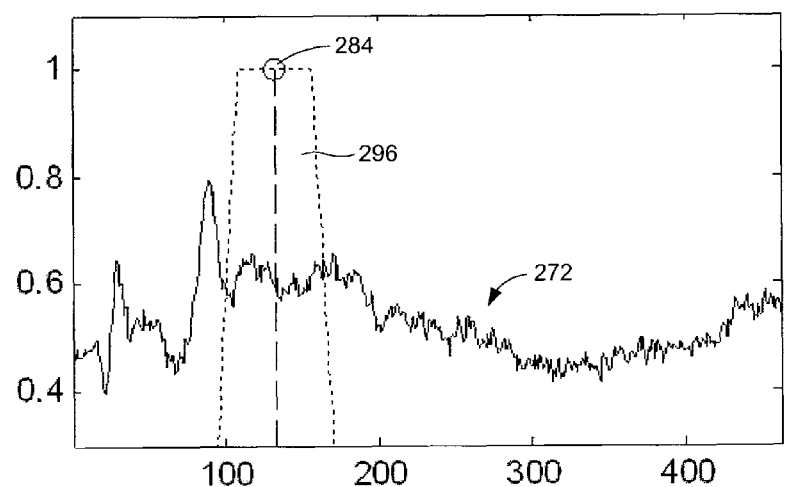
Figure 11B:
Figure 9C:
Figure 10C:
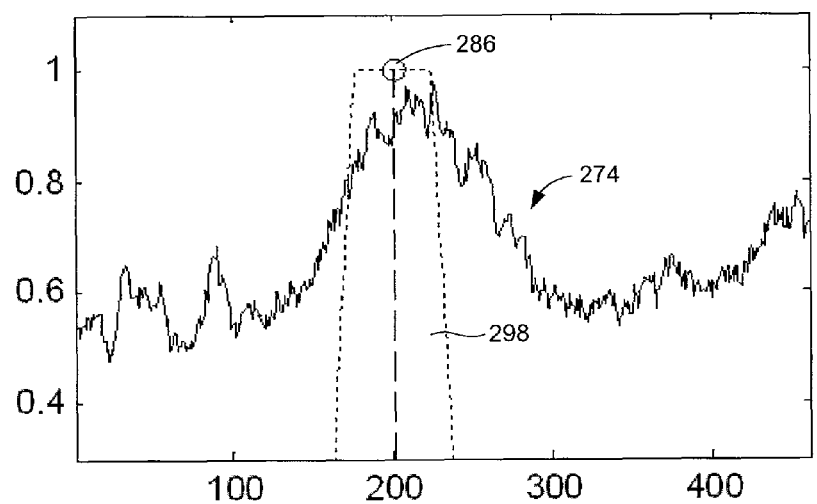
Figure 11C:
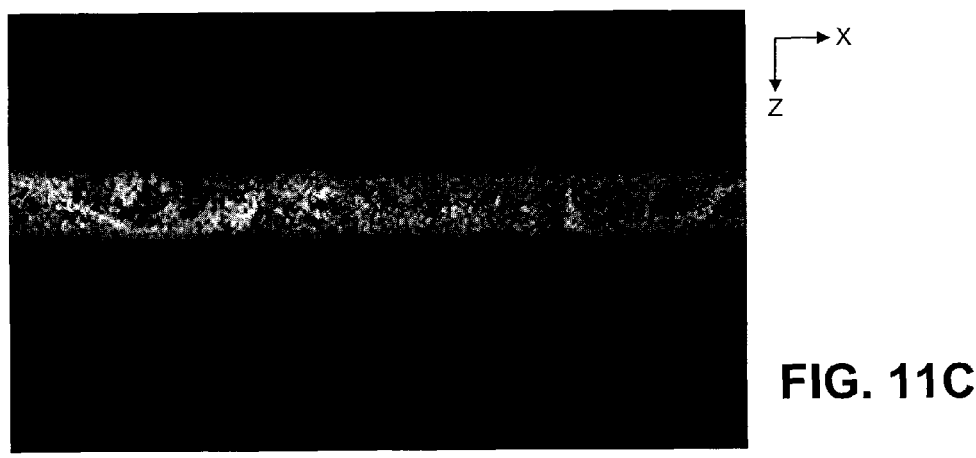
Figure 9D:
Figure 10D:
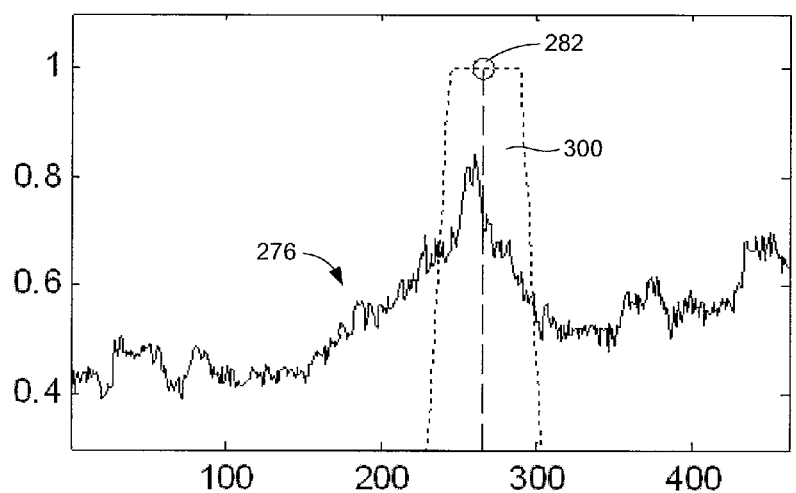
Figure 11D:
Figure 9E:
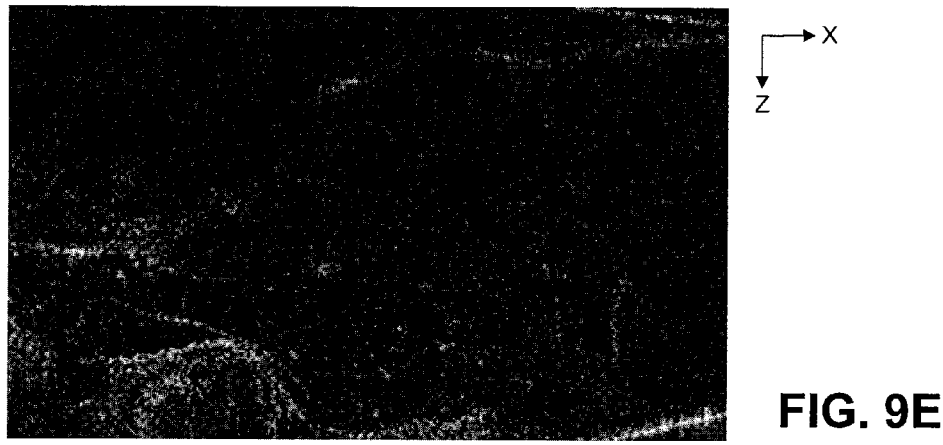
Figure 10E:
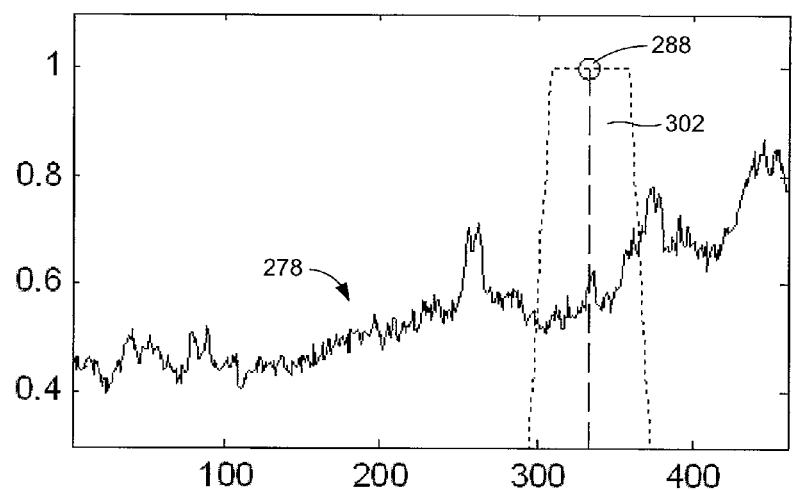
Figure 11E:
Figure 9F:
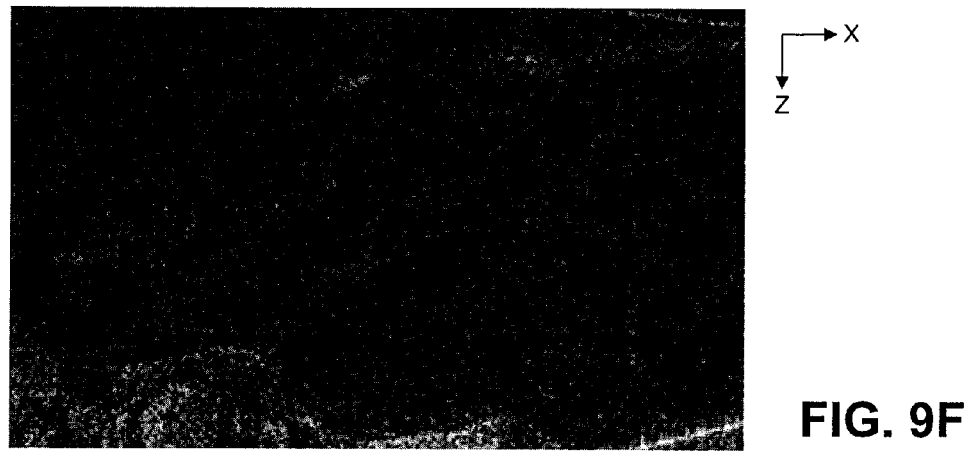
Figure 10F:
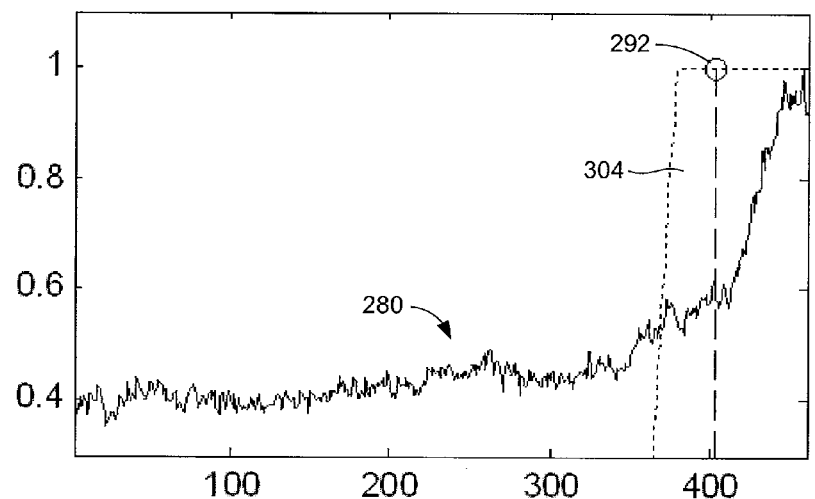
Figure 11F:
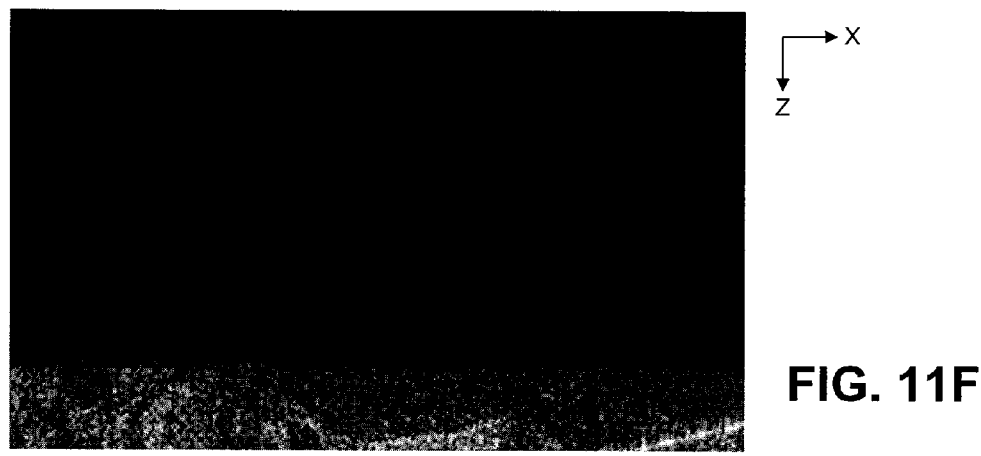

FIG. 8 describes an example method for computing sliding windows. Beginning with block 250 of FIG. 8, a window transition length is first defined. The window translation length is associated with boundary of the window and how quickly it transitions from unity to zero. Stated another way, the transition length is a measure of the slope of the window boundary (see discussion of FIGS. 13 and 10A-10F below).

Referring next to block 252 of FIG. 8, an acquired image is input. The acquired image is then averaged along the lateral scan to obtain the average reflectivity profile as a function of depth. The averaged reflectivities are plotted as reflectivity profiles 270-280 for each acquired image (FIGS. 9A-9F) in FIGS. 10A-10F. In FIGS. 10A-10F, the y-axis is reflectivity and the x-axis is medium depth in terms of sensor pixels along the depth direction. Once the reflectivity profile has been generated, the center of mass, or centroid, of each reflectivity profile can be calculated, as indicated in block 256 of FIG. 8. The positions of the centroids are identified by circles 282-292 (and vertical dashed lines) in FIGS. 10A-10F. As can be appreciated from those figures, the locations of the centroids 282-292 correspond to the depths at which the reflectivity, and therefore focus, is greatest. The centroids 282-292 can be calculated using $$z_C = \frac{\sum_i z_i \cdot r(z_i)}{\sum_i r(z_i)}. \quad (7)$$

where $z_C$ is the centroid and $r(z)$ is the averaged reflectivity profile.

Figure 13:
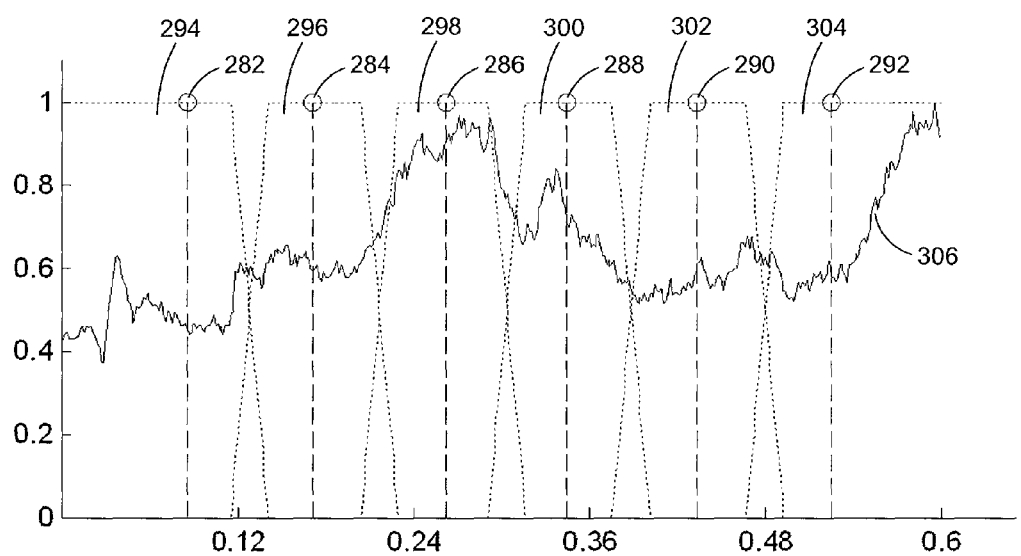
FIG. 13 is an averaged reflectivity profile for the fused image of FIG. 12.

Referring next to decision block 258 of FIG. 8, it is determined whether each acquired image has been processed in the manner described above in relation to blocks 254 and 256. If not, flow returns to block 252 and the next acquired image is processed. If so, however, flow continues down to block 260 and the halfway points between adjacent centroids 282-292 are determined. That is, the position in the depth direction that is halfway between each adjacent pair of centroids is determined. Once those halfway points are known, the window locations can be determined. This process is apparent from FIG. 13, which plots each of the centroids 282-292 from each reflectivity profile 270-280. As depicted in FIG. 13, the boundaries of adjacent windows 294-304 intersect at the halfway points between the centroids 282-292. Because the transition length (slope) was initially defined (block 250 in FIG. 8), the location and expanse of each window 294-304 can be determined using the halfway points. Those locations and expanses are illustrated in FIGS. 10A-10F. As is apparent from those figures, the windows 294-304, like the centroids 282-292, correspond to the medium depths at which the reflectivity, and therefore focus, is greatest. In this example, each window 294-304 has a flat top at unity and is generally trapezoidal.

Figure 12:
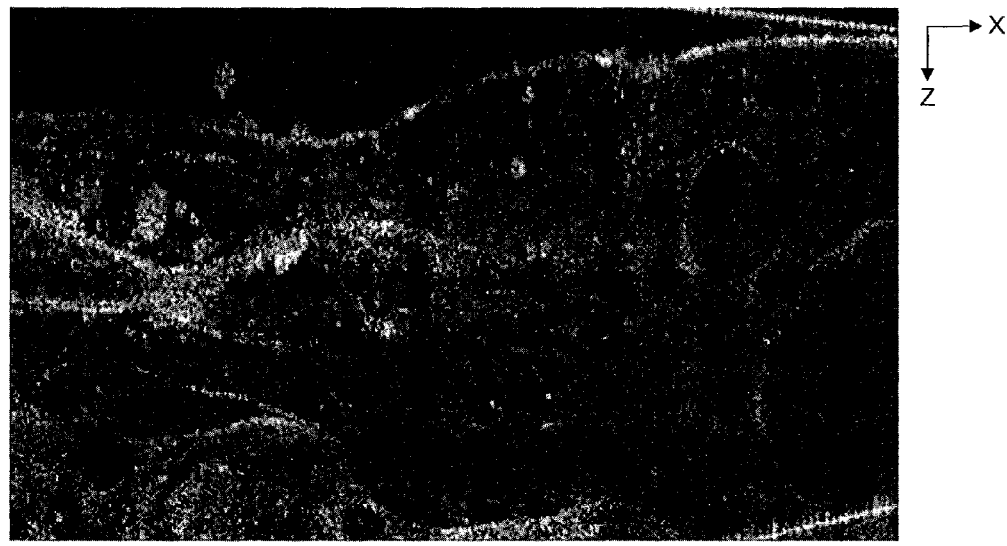
FIG. 12 is a high-resolution fused image that results from merging of the filtered images of FIGS. 10A-10F.

After the windows 294-304 have been computed in the manner described in relation to FIG. 8, the windows can be applied to the acquired images, as indicated in block 236 of FIG. 7. Specifically, the image data of each acquired image can be multiplied by its associated window 294-304. The effect of such multiplication is to maintain the image data that coincides with the window and to nullify or filter out the image data outside of the window. FIGS. 11A-11F are filtered images that result after application of the windows 294-304. As can be appreciated from FIGS. 11A-11F, the filtered images each comprise a discrete portion or band of in-focus image data, which pertains to a given depth of the medium. Once the filtered images have been generated, they can be merged to form a final high-resolution fused image, as indicated in block 238 of FIG. 7. FIG. 12 is the result of such merging. As can be appreciated from FIG. 12, the fused image combines the in-focus portions or bands of each filtered image, and therefore is in focus throughout the image. By way of example, the fused image has an invariant resolution of less than approximately 5 μm. FIG. 13 provides the averaged reflectivity profile 306 for the fused image of FIG. 12. As can be appreciated from FIG. 13, the profile 306 generally comprises the portion of each reflectivity profile within the window of each acquired image (compare FIGS. 10A-10F).

While particular embodiments have been disclosed in detail in the foregoing description and drawings for purposes of example, those skilled in the art will appreciate that variations and modifications may be made without departing from the scope of the disclosure. All such variations and modifications are intended to be included within this disclosure. While this disclosure has focused on two-dimensional images, it is noted that three-dimensional imaging may be achieved through aggregation of the two-dimensional image data.

Various programs (i.e. logic) have been disclosed. Those programs can be stored on any computer-readable medium for use by or in connection with any computer or computer-related system or method. In the context of this disclosure, a computer-readable medium is an electronic, magnetic, optical, or other physical device or means that contains or stores computer instructions.

We claim:

1. A method for imaging a medium under evaluation, the method comprising:
    generating acquired images of the medium, each acquired image comprising a cross-sectional image of the medium along a lateral direction and a depth direction of the medium that results from scanning the medium at discrete depths;
    filtering each acquired image to remove out-of-focus portions of the images and to generate filtered images, wherein filtering comprises computing windows that can be applied to the acquired images to define the portions of the acquired images that will be removed; and
    merging the filtered images to form a high-resolution fused image.

2. The method of claim 1, further comprising scanning the medium using an optical instrument that is applied to a surface of the medium.

3. The method of claim 2, wherein scanning comprises laterally scanning the medium at each discrete depth.

4. The method of claim 3, wherein laterally scanning the medium comprises focusing at a first depth, performing a lateral scan, refocusing on a second depth using a variable focus lens that focuses without mechanical translation, and performing a further lateral scan.

5. The method of claim 1, wherein generating acquired images comprises Fourier transforming spectra acquired during the scanning.

6. The method of claim 1, wherein computing windows comprises, as to each acquired image, averaging the acquired image along the lateral direction to obtain an average reflectivity profile.

7. The method of claim 6, wherein computing windows further comprises calculating the centroid of each average reflectivity profile.

8. The method of claim 7, wherein computing windows further comprises determining halfway points between the adjacent centroids.

9. The method of claim 8, wherein computing windows further comprises defining a window transition length and intersecting the windows at the halfway points to determine the window locations.

10. The method of claim 1, further comprising applying the windows to the acquired images to generate the filtered images.

11. The method of claim 10, wherein applying the windows comprises multiplying each acquired image by its computed window.

12. The method of claim 10, wherein each filtered image comprises a discrete band of in-focus image data associated with a discrete range of depth of the medium.

13. The method of claim 1, wherein the high-resolution fused image has an invariant resolution of less than approximately 3 μm.

14. A non-transitory computer-readable medium that stores an image processing system, the system comprising:
    logic configured to generate acquired images of a medium under evaluation, each acquired image comprising a cross-sectional image of the medium under evaluation along a lateral direction and a depth direction of the medium under evaluation that results from scanning at discrete depths;
    logic configured to filter each acquired image to remove out-of-focus portions of the images and to generate filtered images, the filtering comprising computing windows that can be applied to the acquired images to define the portions of the acquired images that will be removed; and
    logic configured to merge the filtered images to form a high-resolution fused image.

15. The non-transitory computer-readable medium of claim 14, wherein the logic configured to generate acquired images comprises logic configured to Fourier transform spectra acquired during the scanning.

16. The non-transitory computer-readable medium of claim 14, wherein the logic configured to compute windows comprises logic configured to average each acquired image along the lateral direction to obtain an average reflectivity profile.

17. The non-transitory computer-readable medium of claim 16, wherein the logic configured to compute windows further comprises logic configured to calculate the centroid of each average reflectivity profile.

18. The non-transitory computer-readable medium of claim 17, wherein the logic configured to compute windows further comprises logic configured to determine halfway points between the adjacent centroids.

19. The non-transitory computer-readable medium of claim 18, wherein the logic configured to compute windows further comprises logic configured to define a window transition length and logic configured to intersect the windows at the halfway points to determine the window locations.

20. The non-transitory computer-readable medium of claim 14, further comprising logic configured to apply the windows to the acquired images to generate the filtered images.

21. The non-transitory computer-readable medium of claim 20, wherein the logic configured to apply the windows comprises logic configured to multiply each acquired image by its computed window.

22. A method for imaging the skin, the method comprising:
    applying an optical probe to an outer surface of the skin;
    laterally scanning the skin beneath the surface using the optical probe, the scanning comprising performing a lateral scan at a first depth, refocusing at a new depth using a variable focus lens, performing a further lateral scan at the new depth, and repeating the process until a lateral scan has been performed at each of multiple discrete depths;
    collecting spectra resulting from backscattering of light by features within the skin during the scanning;
    Fourier transforming the collected spectra to generate acquired images of the skin, each acquired image comprising a cross-sectional image of the skin taken along a lateral direction and a depth direction;
    filtering each acquired image to remove out-of-focus portions of the images and to generate filtered images, the filtering comprising:
        computing windows that can be applied to the acquired images to define the portions of the acquired images that will be removed,
        individually averaging the acquired images along the lateral direction to obtain an average reflectivity profile for each acquired image,
        calculating the centroid of each average reflectivity profile,
        determining halfway points between the adjacent centroids,
        intersecting the windows at the halfway points to determine the window locations, and
        applying the windows to the acquired images to generate the filtered images; and
    merging the filtered images to form a high-resolution fused image.

23. The method of claim 22, wherein refocusing a variable focus lens comprises refocusing a liquid lens.

24. The method of claim 22, wherein refocusing a variable focus lens comprises refocusing a liquid crystal lens.

25. The method of claim 22, wherein each filtered image comprises a discrete band of in-focus image data associated with a discrete range of depth of the medium.

26. The method of claim 22, wherein the high-resolution fused image has an invariant resolution of less than approximately 3 μm.

* * * * *